(12) United States Patent
Wang et al.

(10) Patent No.: US 10,542,876 B2
(45) Date of Patent: Jan. 28, 2020

(54) MULTIDIRECTIONAL TURNING ENDOSCOPE

(71) Applicant: YOUCARE TECHNOLOGY CO., LTD.(WUHAN), Wuhan, Hubei (CN)

(72) Inventors: Shaogang Wang, Hubei (CN); Xiao Yu, Hubei (CN); Yeyun Mao, Hubei (CN); Zhangqun Ye, Hubei (CN); Jian Huang, Guangdong (CN); Jianxing Li, Beijing (CN); Xu Zhang, Beijing (CN); Jihong Liu, Hubei (CN); Yiran Huang, Shanghai (CN); Lin Qi, Hunan (CN); Xiuheng Liu, Hubei (CN); Xiaoping Zhang, Hubei (CN); Tongzu Liu, Hubei (CN); Kunjie Wang, Sichuan (CN); Xiaolin Guo, Hubei (CN); Qi Chen, Shanghai (CN); Lei Song, Beijing (CN); Yaohui Wu, Hubei (CN); Ying Li, Hubei (CN); Xuecheng Hu, Hubei (CN); Gang Long, Hubei (CN)

(73) Assignee: YOUCARE TECHNOLOGY CO., LTD.(WUHAN), Wuhan, Hubei (CN)

( * ) Notice: Subject to any disclaimer, the term of this patent is extended or adjusted under 35 U.S.C. 154(b) by 368 days.

(21) Appl. No.: 15/533,311

(22) PCT Filed: Jun. 2, 2015

(86) PCT No.: PCT/CN2015/080554
§ 371 (c)(1),
(2) Date: Jun. 5, 2017

(87) PCT Pub. No.: WO2016/192033
PCT Pub. Date: Dec. 8, 2016

(65) Prior Publication Data
US 2017/0325660 A1 Nov. 16, 2017

(51) Int. Cl.
*A61B 1/005* (2006.01)
*A61B 1/00* (2006.01)
(Continued)

(52) U.S. Cl.
CPC .......... *A61B 1/0052* (2013.01); *A61B 1/0055* (2013.01); *A61B 1/0057* (2013.01);
(Continued)

(58) Field of Classification Search
CPC ............... A61B 1/0051; A61B 1/0052; A61M 25/0133; F16C 1/12
(Continued)

(56) References Cited

U.S. PATENT DOCUMENTS

| 4,996,974 A | * | 3/1991 | Ciarlei | A61B 1/0052 138/120 |
| 2002/0165484 A1 | * | 11/2002 | Bowe | A61M 25/0136 604/95.05 |
| 2013/0038930 A1 | * | 2/2013 | Vent | A61B 1/0052 359/362 |

\* cited by examiner

*Primary Examiner* — Aaron B Fairchild

(57) ABSTRACT

The present invention relates to a multidirectional turning endoscope, which includes an insertion portion (2), an endoscope handle (4) and a bending driving portion (3); wherein: the bending driving portion includes a left-right driving rod, an up-down driving rod, a rotation shaft, a left turning wheel (17), a right turning wheel (18) and a spring (19); the rotation shaft includes a left half shaft (15) and a right half shaft (16); the external surface of the left half shaft and the external surface of the right half shaft respectively have a left outer conical face and a right outer conical face, a left conical cylinder and a right conical cylinder (20) are respectively sleeved to the left outer conical face and a right outer conical face; a spring (19) is located at an axial direction of the left half shaft and the right half shaft.

18 Claims, 4 Drawing Sheets

(51) Int. Cl.
    *A61B 1/012* (2006.01)
    *A61M 25/01* (2006.01)
(52) U.S. Cl.
    CPC ...... *A61B 1/00066* (2013.01); *A61B 1/00137* (2013.01); *A61B 1/00147* (2013.01); *A61B 1/012* (2013.01); *A61M 25/0136* (2013.01); *A61M 25/0147* (2013.01)
(58) Field of Classification Search
    USPC .......................................................... 600/148
    See application file for complete search history.

MULTIDIRECTIONAL TURNING ENDOSCOPE

CROSS REFERENCE OF RELATED APPLICATION

This is a U.S. National Stage under 35 U.S.C 371 of the International Application PCT/CN2015/080554, filed Jun. 2, 2015.

BACKGROUND OF THE PRESENT INVENTION

Field of Invention

The present invention relates to medical devices, and more particularly to an endoscope which is capable of multi-directionally turning along an up and down direction and a left and right direction.

Description of Related Arts

Endoscopes are widely used in the industrial and medical fields. It is common to insert the elongated portion into a cavity to observe a location that is invisible to the naked eyes. The medical endoscope is an indispensable and important instrument in medical examination and surgery. The early medical endoscope is rigid, although it is easy to be operated, its front end is unable to be bent for reaching the site with the curved tract. With the progress of science and technology, the flexible and rigid endoscope are gradually produced, in which the front end of the insertion portion is bent by means of controlling the device on the handle and enters the cavity along the curved tract. The fiberoptic endoscope or the electronic endoscope is inserted into the cavity, for transmitting observed images to an external display, thereby achieving the observation, diagnosis and treatment.

Most of the existing flexible medical endoscopes are unidirectional turning or bidirectional turning, and are in need of additional locking devices. The operator holds the endoscope handle by one hand, and controls the operation portion so as to achieve the bending of the bending portion along the up and down direction and the left and right direction. If the operator is unfamiliar with the product or the operator's hand is relatively small, the operator needs to hold the insertion portion with one hand to ensure the position of the insertion portion and needs to control the bending by the other hand in case of a complicated situation. Even for a skilled operator, after finding the target with one hand, a long period of control state after bending shall be maintained, consequently, the operator becomes fatigued easily, and the risk of surgery is increased.

Alternatively, the operator locks the bending state with his or her other hand, and releases the lock if the bending state needs to be changed, which increases the complexity of the operation. In the process of locking and unlocking, the endoscope is likely to cause jitter and lose the target, which is not conducive to the operation.

SUMMARY OF THE PRESENT INVENTION

An object of the present invention is to overcome the drawbacks of the background art described above and to provide a multidirectional turning endoscope which is simple in operation and has the characteristic of stepless self-locking, that is, self-locking at any bending position, thereby achieving high surgical safety.

To achieve the above object, the present invention adopts technical solutions as follows.

A multidirectional turning endoscope comprises an insertion portion, an endoscope handle and a bending driving portion; wherein:

the insertion portion has a curved section at a front end thereof, a back end of the insertion portion is connected with the endoscope handle, two pairs of turning traction wires are located within the insertion portion, the two turning traction wires are connected with the bending driving portion;

the bending driving portion is a self-locking bending driving portion which comprises a left-right driving rod, an up-down driving rod, a rotation shaft, a left turning wheel, a right turning wheel and a spring;

two ends of the rotation shaft are respectively located within positioning holes in two opposite inner walls of the endoscope handle, and the rotation shaft has a gap in each of the positioning holes along an axial direction thereof;

the rotation shaft comprises a left half shaft and a right half shaft which are coaxially connected with each other and capable of independently turning;

the left turning wheel and the right turning wheel are respectively fixed to an external surface of the left half shaft and the right half shaft;

two back ends of one pair of the turning traction wires are respectively spacedly fixed along a circumferential direction of the left turning wheel, and two back ends of another pair of the turning traction wires are respectively spacedly fixed along a circumferential direction of the right turning wheel;

the external surface of the left half shaft and the external surface of the right half shaft respectively have a left outer conical face and a right outer conical face which are coaxially aligned with the rotation shaft, a left conical cylinder and a right conical cylinder are respectively sleeved to the left outer conical face and a right outer conical face, the left conical cylinder and the right conical cylinder respectively match with the left outer conical face and the right outer conical face, and the left conical cylinder and the right conical cylinder are respectively fixed to an inner wall of the endoscope handle;

a spring, which is capable of driving the left half shaft to move towards a direction of the left conical cylinder, driving the right half shaft to move towards a direction of the right conical cylinder, forcing the left outer conical face to closely fitted with the left conical cylinder for self-locking, and forcing the right outer conical face to closely fitted with the right conical cylinder for self-locking, is located at an axial direction of the left half shaft and the right half shaft; and the left-right driving rod and the up-down driving rod are respectively connected with an outer end of the left half shaft and an outer end of the right half shaft.

Preferably, the left half shaft and the right half shaft are connected with each other along an axial direction thereof in a cooperating manner of round pin shaft and round pin hole.

Preferably, the left outer conical face and the right outer conical face are respectively provided at the left half shaft and the right half shaft which are located outside the left turning wheel and the right turning wheel; the spring is sleeved to a joint of the left half shaft and the right half shaft, and two ends of the spring respectively are placed against two opposite end surfaces of the left turning wheel and the right turning wheel.

Preferably, the left outer conical face and the right outer conical face are respectively located at a surface of the left outer conical sleeve and a surface of the right outer conical sleeve, a big end of the left outer conical sleeve and a big end of the right outer conical sleeve are respectively integrally formed with the end surface of the left turning wheel and the end surface of the right turning wheel to form integral structures, and the integral structures are respectively sleeved and fixed to the left half shaft and the right half shaft.

Preferably, the left conical cylinder or the right conical cylinder is threadedly connected with the inner wall of the endoscope handle, an external surface of the left conical cylinder or the right conical cylinder has external screw threads, the inner wall of the endoscope handle has internal threaded holes, and the external screw threads of the left or right conical cylinder are engaged with the internal threaded holes.

Preferably, two back ends of one pair of the turning traction wires are respectively fixed along the circumferential directions of the left turning wheel with an interval of 180°, and two back ends of another pair of the turning traction wires are respectively fixed along the circumferential directions of the right turning wheel with an interval of 180°.

Preferably, the insertion portion is a flexible sheath;

a cap is located at a front end of the flexible sheath;

the flexible sheath has multiple channels therein along an axial direction thereof, including two pairs of traction channels, two traction channels of each pair are distributed symmetrically relative to a center of the flexible sheath, a connecting line of the two traction channels of each pair passes through a circle center of the flexible sheath, and the two pairs of traction channels are distributed in a cross manner;

the flexible sheath comprises a base part located at a back and a curved part located at a front, capillary support tubes are respectively located within the traction channels at the base part of the flexible sheath;

the turning traction wires respectively pass through the traction channels and the capillary support tubes and then are connected with the cap.

Preferably, the insertion portion comprises a flexible sheath and a rigid sheath, wherein: the flexible sheath is inserted into the rigid sheath;

a cap is located at a front end of the flexible sheath;

the flexible sheath has multiple cavities therein along an axial direction thereof, the multiple cavities comprise two pairs of traction channels, two traction channels of each pair are distributed symmetrically relative to a center of the flexible sheath, a connecting line of the two traction channels of each pair passes through a circle center of the flexible sheath, and the two pairs of traction channels are distributed in a cross manner;

the turning traction wires respectively pass through the traction channels and then are connected with the cap.

The invention has the advantages of reliable positioning, simple structure and convenient processing and assembling. Especially, the present invention adopts the special self-locking bending driving portion, through adjusting the engagement depth between the left or right conical cylinder and the inner wall of the endoscope handle, the compression degree and the restoring force of the spring are adjusted, so as to respectively closely fit the left outer conical face on the left half shaft with the inner conical face of the left conical cylinder, and closely fit the right outer conical face on the right half shaft with the inner conical face of the right conical cylinder, so that the friction force therebetween is balanced with the restoring force of the spring, thereby achieving self-locking. Through the structure described above, the flexible sheath is capable of being locked stepless at any position while bending left and right, so as to meet the requirements of endoscopic free positioning during surgery, reduce the labor intensity of the surgical process, and prevent patient injury caused by misoperation.

The present invention is designed according to ergonomic principles and is able to meet the requirement of the doctor to operate the endoscope with one hand so that the swinging handle angle corresponds to the bending angle of the flexible sheath, the doctor is able to clearly perceive and control the soft sheath bending during the operation, to achieve the required bending angle.

The endoscope according to the present invention is able to control the left-right direction driving rod and the front-rear direction driving rod, so as to realize the front-rear and left-right multidirectional bending of the insertion part of the endoscope, and stepless self-lock in any direction.

DETAILED DESCRIPTION OF THE PREFERRED EMBODIMENT

Figure 1:
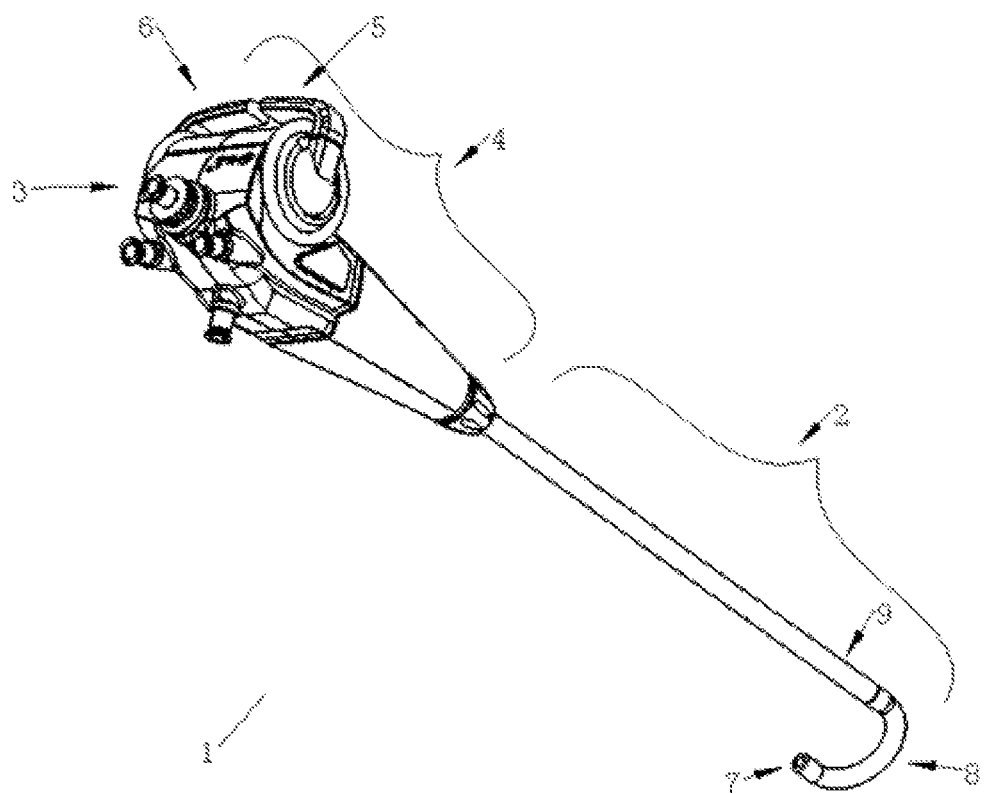
FIG. 1 is a perspective view of a multidirectional turning endoscope according to a first preferred embodiment of the present invention.

The present invention is further explained in detail with accompanying drawings which are not the limitation to the present invention and only the examples.

Embodiment 1

Referring to FIGS. 1-6, a multidirectional turning endoscope 1 according to a first preferred embodiment of the present invention is illustrated, which comprises an insertion portion 2, an endoscope handle 4 and a bending driving portion 3; wherein: the insertion portion 2 has a curved section at a front end thereof, a back end of the insertion portion 2 is connected with the endoscope handle 4, two pairs of turning traction wires 10.1, 10.2 and 10.3, 10.4 are located within the insertion portion 2 and connected with the bending driving portion 3.

Figure 2:
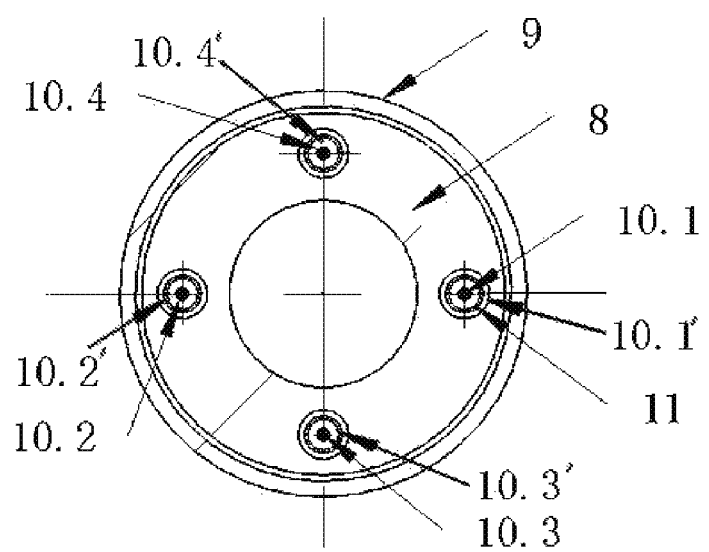
FIG. 2 is a radially sectional view of an insertion portion of the multidirectional turning endoscope in FIG. 1.
Figure 3:
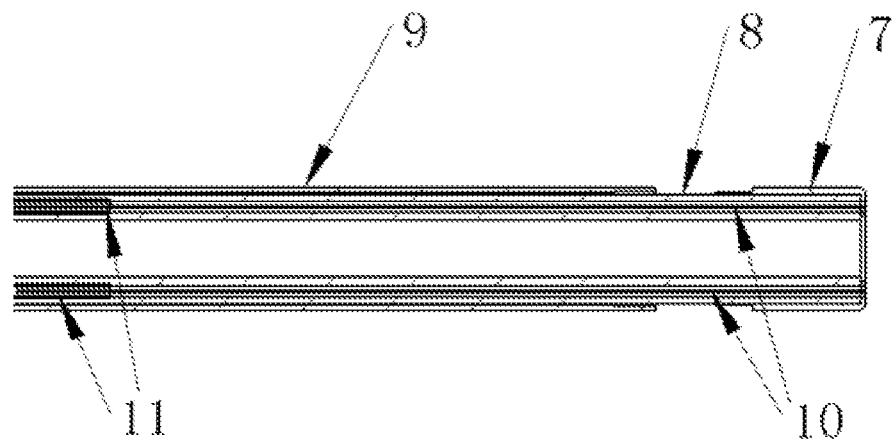
FIG. 3 is an axially sectional view of the insertion portion of the multidirectional turning endoscope in FIG. 1.
Figure 4:
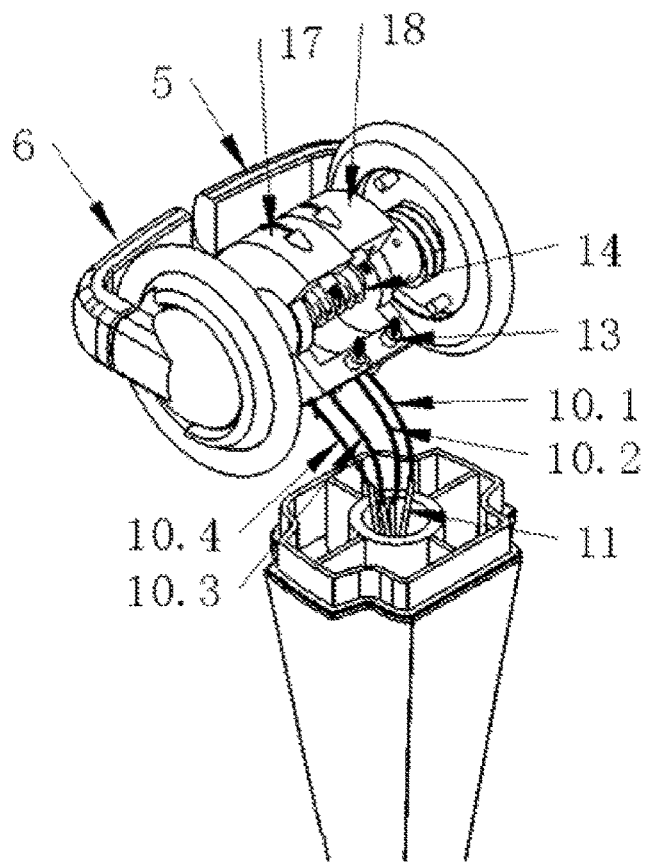
FIG. 4 is a perspective view of a bending driving portion of the multidirectional turning endoscope in FIG. 1.

In the first preferred embodiment, the insertion portion 2 comprises a flexible sheath 8 and a rigid sheath 9, wherein: the flexible sheath 8 is inserted into the rigid sheath 9; a cap 7 is located at the front end of the flexible sheath 8; the flexible sheath 8 has multiple channels therein along an axial direction thereof, including two pairs of traction channels 10.1', 10.2' and 10.3', 10.4', two traction channels of each pair are distributed symmetrically relative to a center of the flexible sheath 8, a connecting line of the two traction channels of each pair passes through a circle center of the flexible sheath 8, and the two pairs of traction channels are distributed in a cross manner; the flexible sheath 8 comprises a base part located at a back and a curved part located at a front, capillary support tubes 11 are respectively located within the traction channels at the base part of the flexible sheath 8; the turning traction wires 10 (including 10.1, 10.2, 10.3 and 10.4) respectively pass through the traction channels and the capillary support tubes 11, a front end of each of the turning traction wires is connected with the cap 7, a back end of each of the turning traction wires is connected with the bending driving portion, as shown in FIGS. 2 and 3.

The cap 7 is made of hard medical materials (which comprise 304 stainless steel and various polymer materials). The cap 7 has a hole therein which is corresponding to the flexible sheath 8. An objective lens is blocked by a front end of the cap 7, unabling to pass through the cap 7. Images observed by the objective lens are converted into electrical signals and finally showed on a display. The cap 7 further has an instrument exit through which various medical instruments or gas and water reach a destination.

The bending driving portion 3 is a self-locking bending driving portion which comprises a left-right driving rod 5, an up-down driving rod 6, a rotation shaft, a left turning wheel 17, a right turning wheel 18 and a spring 19; wherein: two ends of the rotation shaft are respectively located within positioning holes in two opposite inner walls of the endoscope handle for axially positioning, and the rotation shaft has a gap in each of the positioning holes along an axial direction thereof for allowing the rotation shaft to axially move within the gap; the rotation shaft comprises a left half shaft 15 and a right half shaft 16 which are coaxially connected with each other along an axial directional thereof in a cooperating manner of round pin shaft and round pin hole, and are capable of independently turning. In this first preferred embodiment, the round pin shaft is located at an end portion of the right half shaft 16 and is coaxially aligned with the right half shaft 16; the round pin hole is provided in an end portion of the left half shaft 15 and is coaxially aligned with the left half shaft 15, the round pin shaft is inserted into the round pin hole.

Figure 5:
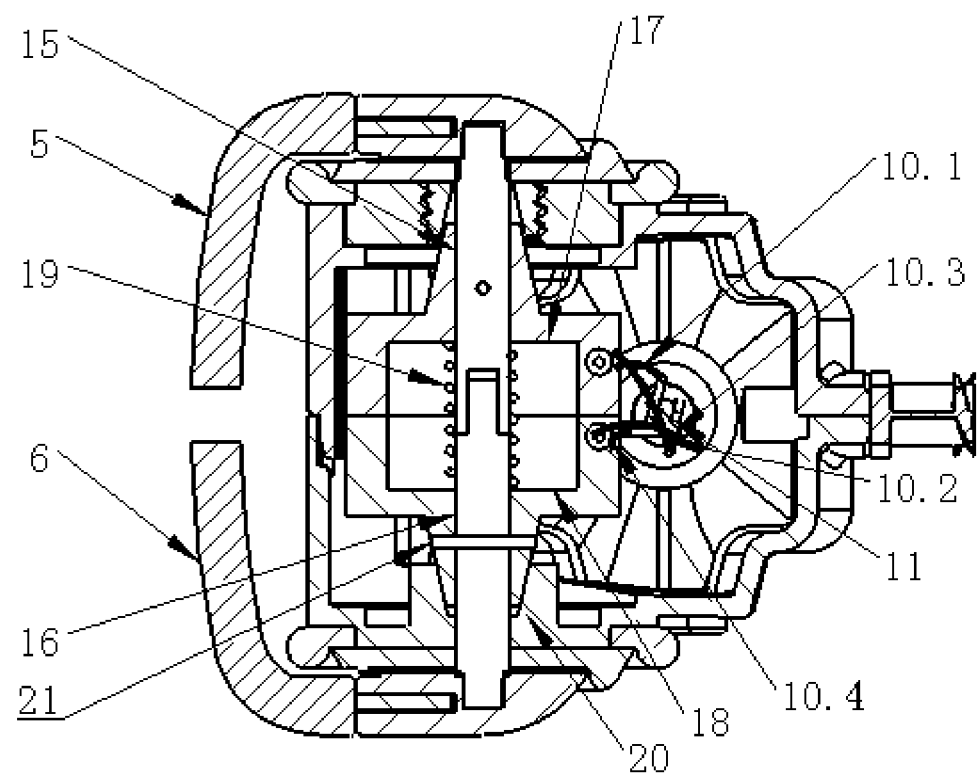
FIG. 5 is a sectional view of FIG. 4 along an axial direction of a rotation shaft.
Figure 6:
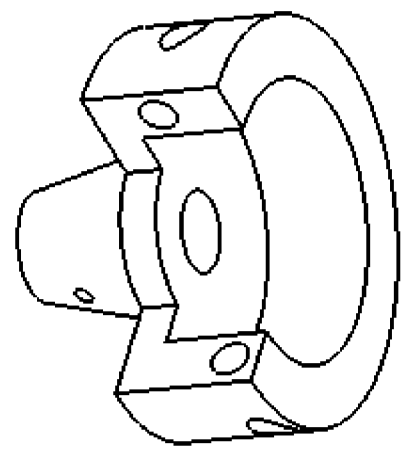
FIG. 6 is a structurally schematic view of a left and right turning wheel.
Figure 7:
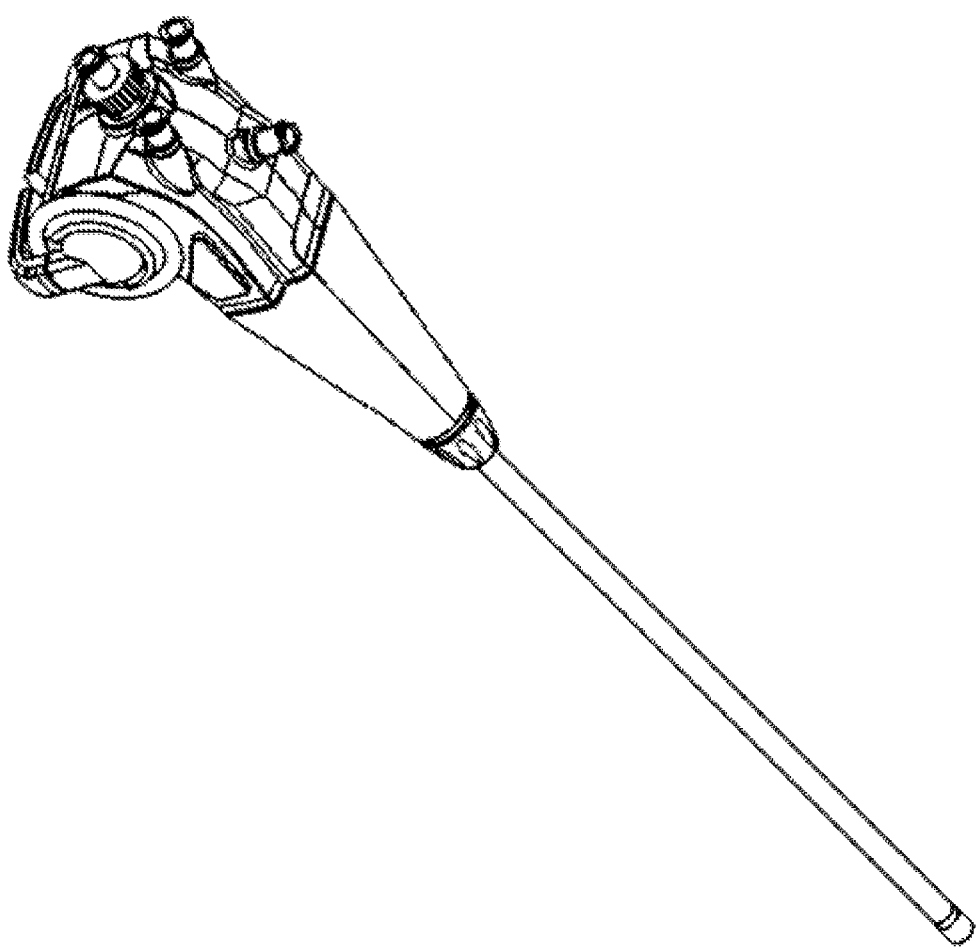
FIG. 7 is perspective view of a multidirectional turning endoscope according to a second preferred embodiment of the present invention.

The left turning wheel 17 and the right turning wheel 18 are respectively fixed to an external surface of the left half shaft 15 and the right half shaft 16; two back ends of one pair of the turning traction wires 10 are respectively fixed along the circumferential directions of the left turning wheel 17 with an interval of 180°, and two back ends of another pair of the turning traction wires 10 are respectively fixed along the circumferential direction of the right turning wheel 18 with an interval of 180°, as shown in FIG. 5.

A left outer conical sleeve and a right outer conical sleeve respectively have a left outer conical face and a right outer conical face 21 on a surface thereof; the left outer conical face and the right outer conical face 21, which are coaxially aligned with the rotation shaft, are respectively provided at the external surface of the left half shaft 15 and the external surface of the right half shaft 16; a big end of the left outer conical sleeve and a big end of the right outer conical sleeve are respectively integrally formed with an end surface of the left turning wheel 17 and an end surface of the right turning wheel 18 to form integral structures, and the integral structures are respectively sleeved to the left half shaft and the right half shaft and fixed therewith through pins, as shown in FIG. 5.

A left conical cylinder and a right conical cylinder 20 are respectively sleeved to the left outer conical face and a right outer conical face 21, the left conical cylinder and a right conical cylinder respectively matches with the left outer conical face and a right outer conical face 21, and the left conical cylinder and the right conical cylinder are respectively fixed to the two opposite inner walls of the endoscope handle. A spring 19 is sleeved to a joint of the left half shaft 15 and the right half shaft 16, and two ends of the spring 19 respectively are placed against two opposite end surfaces of the left turning wheel 17 and the right turning wheel 18.

In this first preferred embodiment, any one of the left or right conical cylinder is threadedly connected with an inner wall of the endoscope handle, an external surface of the left conical cylinder or the right conical cylinder has external screw threads, the inner wall of the endoscope handle 4 has internal threaded holes, and the external screw threads of the left or right conical cylinder are engaged with the internal threaded holes.

The spring 19 is capable of driving the left half shaft to move towards a direction of the left conical cylinder and driving the right half shaft to move towards a direction of the right conical cylinder. Through adjusting an engagement depth between the left or right conical cylinder and inner thread screw holes in the inner wall of the endoscope handle 4, a compression degree and a restoring force of the spring 19 are adjusted, so as to respectively closely fit the left outer conical face with the left conical cylinder, and closely fit the right outer conical face with the right conical cylinder, thereby achieving self-locking. Through the structure described above, it is ensured that a head portion of the flexible sheath 8 is capable of self-locking stepless at any position while bending up and down. Similarly, the head portion of the flexible sheath 8 is capable of self-locking stepless at any position while bending left and right.

The left-right driving rod 5 and the up-down driving rod 6 are respectively connected with an outer end of the left half shaft and an outer end of the right half shaft.

Embodiment 2

As shown in FIGS. 4-7, a multidirectional turning endoscope according to a second preferred embodiment of the present invention is illustrated, which is basically same with the multidirectional turning endoscope according to the first embodiment of the present invention. Differences therebetween are as follows. An insertion portion 2 comprises a flexible sheath 8 (not shown in the drawings). A cap 7 is located at a front end of the flexible sheath 8; the flexible sheath 8 has multiple channels therein along an axial direction thereof, including two pairs of traction channels, two traction channels of each pair are distributed symmetrically relative to a center of the flexible sheath, a connecting line of the two traction channels of each pair passes through a circle center of the flexible sheath 8, and the two pairs of traction channels are distributed in a cross manner; the flexible sheath comprises a base part located at a back and a curved part located at a front, and capillary support tubes 11 are respectively located within the traction channels at the base part of the flexible sheath.

In the two embodiments described above, after each of the turning traction wires 10 passes through a corresponding traction channel and a corresponding capillary support tube 11, a back end of each of the turning traction wires is fixed to installation holes of the left turning wheel 17 and the right turning wheel 18 through adjustment of screws 13. Two symmetrical turning traction wires 10.1 and 10.2 of one pair wind around the right turning wheel 18, and control a front end of the flexible sheath 8 to turn left and right through the left-right driving rod 5. Two symmetrical turning traction wires 10.3 and 10.4 of another pair wind around the left turning wheel 17, and control the front end of the flexible sheath 8 to turn up and down through the up-down driving rod 6.

The present invention drives the left half shaft to turn through operating the left-right driving rod 5, and simultaneously, drive the left turning wheel 17 on the left half shaft to turn, so as to tighten one turning traction wire of one pair 10 fixed to the left turning wheel 17 and loosen another turning traction wire of one pair 10, for controlling the front end of the flexible sheath 8 to turn left and right; similarly, the present invention is capable of driving the front end of the flexible sheath 8 to turn up and down through operating the up-down driving rod 6. Through the mechanism mentioned above, the flexible sheath is able to be locked stepless at any position, and simultaneously, the endoscope is able to be operated with one hand to reduce the burden on doctors.

The endoscope provided by the present invention has excellent reliability, accurate position, simple structure and convenient assembly.

The following is a brief summary of the several conventional applications of the present invention.

1. Urological application: The multidirectional turning endoscope provided by the present invention is able to be used for ureteroscopes, and optimize the current cystoscopes and percutaneous nephroscopes, effectively reduce doctors' surgical strength, and increase the surgical precision. Furthermore, it is also able to be applied to the treatment of kidney stones, bladder stones, renal cysts, and renal tumors.

2. Application in neurosurgery: The multidirectional turning endoscope provided by the present invention is able to ensure a safe and reliable operation, and be widely used for the treatment of hydrocephalus, intraventricular disease, skull base surgery, pituitary tumor, aneurysm, intracranial hematoma, and subdural hematoma, and in particular, separated subdural hematoma and endoscopic percutaneous discectomy, and even for brain parenchyma tumor biopsy and small tumor resection, trigeminal microvascular decompression and vestibular nerve section and so on.

3. Application in gynecology: The multidirectional turning endoscope provided by the present invention is able to be used in the falloposcope, optimizing the present hysteroscope, laparoscope and colposcope; and it is also able to be used for clinical patient with precancerous cervical lesions or suspicious cervical cancer, person with abnormal cells found in anti-cancer pictures, and cervical lesions after follow-up treatment, so as to understand the treatment effect whether recurrence or new lesions occur, abnormal uterine bleeding, uterine fibroids, polyps and endometrial cancer, abnormal ultrasound sound and video findings, infertility and family planning complications, hormone replacement and application of tamoxifen induced endometrial physiological or special changes, previous IVF (in vitro fertilization) failing patients; to replace hysteroscopy to check endometrial conditions, habitual abortion, to see whether the uterine cavity is normal, metrosynizesis, foreign bodies in uterine cavity, and to cut benign gynecologic tumors, diagnose and treat exfetation, treat oophoritic cyst, strip pelvic adhesions, burn endometriosis and ligature oviduct and so on.

4. Application in general surgery: The multidirectional turning endoscope provided by the present invention is able to be used in laparoscopes including various optimized laparoscopes such as the HD type and the ultrafine type, which is applicable not only to external open channels but also to various natural orifices. Ultra-high clarity and ultra-large field of view angle are able to help doctors to more clearly observe a wider position in the abdominal cavity, so as to rapidly identify and treat the lesion. Also, the ultra-fine laparoscope is used in laparoscopic surgery, that is to say, that after the small surgical channel is opened in the patient's abdominal cavity, based on the turning characteristic of the soft sheath, the ultra-fine laparoscope is able to reach the positions where the general endoscopes are unable to reach, thereby reducing the amount of openings and the damage to the patient.

In addition, the multidirectional turning endoscope provided by the present invention is also able to be used in surgical treatment of liver, biliary tract, pancreas, stomach and intestine, anorectum, vascular diseases, thyroid and breast tumors and trauma and other diseases.

The foregoing is intended to be illustrative of the preferred embodiments of the present invention and is not intended to limit the structure of the present invention in any way. Any simple modifications, equivalent changes and modifications to the above embodiments in accordance with the technical essence of the present invention are within the scope of the present invention.

What is claimed is:

1. A multidirectional turning endoscope, comprising an insertion portion (2), an endoscope handle (4) and a bending driving portion (3); wherein:

the insertion portion (2) has a curved section at a front end thereof, a back end of the insertion portion (2) is connected with the endoscope handle (4), two pairs of turning traction wires (10) are located within the insertion portion (2), the two pairs of the turning traction wires are connected with the bending driving portion (3);

the bending driving portion (3) is a self-locking bending driving portion which comprises a left-right driving rod (5), an up-down driving rod (6), a rotation shaft, a left turning wheel (17), a right turning wheel (18) and a spring (19);

two ends of the rotation shaft are respectively located within positioning holes in two opposite inner walls of the endoscope handle (4), and the rotation shaft has a gap in each of the positioning holes along an axial direction of the each of the positioning holes;

the rotation shaft comprises a left half shaft (15) and a right half shaft (16) which are coaxially connected with each other and capable of independently turning;

the left turning wheel (17) and the right turning wheel (18) are respectively fixed to an external surface of the left half shaft (15) and the right half shaft (16);

two back ends of one pair of the turning traction wires (10) are respectively spacedly fixed along a circumferential direction of the left turning wheel (17), and two back ends of another pair of the turning traction wires (10) are respectively spacedly fixed along a circumferential direction of the right turning wheel (18);

the external surface of the left half shaft (15) and the external surface of the right half shaft (16) respectively have a left outer conical face and a right outer conical face (21) which are coaxially aligned with the rotation shaft, a left conical cylinder and a right conical cylinder (20) are respectively sleeved to the left outer conical face and a right outer conical face (21), the left conical cylinder and the right conical cylinder (20) respectively match with the left outer conical face and the right outer conical face (21), and the left conical cylinder and the right conical cylinder (20) are respectively fixed to an inner wall of the endoscope handle (4);

a spring (19), which is capable of driving the left half shaft to move towards a direction of the left conical cylinder, driving the right half shaft to move towards a direction of the right conical cylinder, forcing the left outer conical face to closely fit with the left conical cylinder for self-locking, and forcing the right outer conical face to closely fit with the right conical cylinder for self-locking, is provided along an axial direction of the left half shaft (15) and the right half shaft (16); and the left-right driving rod (5) and the up-down driving rod (6) are respectively connected with an outer end of the left half shaft (15) and an outer end of the right half shaft (16).

2. The multidirectional turning endoscope, as recited in claim 1, wherein: the left half shaft (15) and the right half shaft (16) are connected with each other along an axial direction thereof in a cooperating manner of round pin shaft and round pin hole.

3. The multidirectional turning endoscope, as recited in claim 2, wherein:

the insertion portion (2) is a flexible sheath (8);

a cap (7) is located at a front end of the flexible sheath (8);

the flexible sheath (8) has multiple channels therein along an axial direction thereof, including two pairs of traction channels, two traction channels of each pair are distributed symmetrically relative to a center of the flexible sheath (8), a connecting line of the two traction channels of each pair passes through a circle center of the flexible sheath (8), and the two pairs of traction channels are distributed in a cross manner;

capillary support tubes (11) are respectively located within the two pairs of traction channels of the flexible sheath (8);

the turning traction wires (10) pass through the traction channels and the capillary support tubes (11) and then are connected with the cap (7).

4. The multidirectional turning endoscope, as recited in claim 2, wherein:

the insertion portion (2) comprises a flexible sheath (8) and a rigid sheath (9);

the flexible sheath (8) is inserted into the rigid sheath (9);

a cap (7) is located at a front end of the flexible sheath (8);

the flexible sheath (8) has multiple channels therein along an axial direction thereof, including two pairs of traction channels, two traction channels of each pair are distributed symmetrically relative to a center of the flexible sheath (8), a connecting line of the two traction channels of each pair passes through a circle center of the flexible sheath (8), and the two pairs of traction channels are distributed in a cross manner;

the turning traction wires (10) pass through the traction channels and then are connected with the cap (7).

5. The multidirectional turning endoscope, as recited in claim 1, wherein: the left outer conical face and the right outer conical face are respectively provided at the left half shaft (15) and the right half shaft (16) which are located outside the left turning wheel (17) and the right turning wheel (18);

the spring (19) is sleeved to a joint of the left half shaft (15) and the right half shaft (16), and two ends of the spring (19) respectively are placed against an end surface of the left turning wheel (17) and an end surface of the right turning wheel (18) which is opposite to the end surface of the left turning wheel (17).

6. The multidirectional turning endoscope, as recited in claim 5, wherein: the left outer conical face and the right outer conical face (21) are respectively provided at a surface of a left outer conical sleeve and a surface of a right outer conical sleeve, a big end of the left outer conical sleeve and a big end of the right outer conical sleeve are respectively integrally formed with the end surface of the left turning wheel (17) and the end surface of the right turning wheel (18) to form integral structures, and the integral structures are respectively sleeved and fixed to the left half shaft (15) and the right half shaft (16).

7. The multidirectional turning endoscope, as recited in claim 6, wherein:

the insertion portion (2) is a flexible sheath (8);

a cap (7) is located at a front end of the flexible sheath (8);

the flexible sheath (8) has multiple channels therein along an axial direction thereof, including two pairs of traction channels, two traction channels of each pair are distributed symmetrically relative to a center of the flexible sheath (8), a connecting line of the two traction channels of each pair passes through a circle center of the flexible sheath (8), and the two pairs of traction channels are distributed in a cross manner;

capillary support tubes (11) are respectively located within the two pairs of traction channels of the flexible sheath (8);

the turning traction wires (10) pass through the traction channels and the capillary support tubes (11) and then are connected with the cap (7).

8. The multidirectional turning endoscope, as recited in claim 6, wherein:

the insertion portion (2) comprises a flexible sheath (8) and a rigid sheath (9);

the flexible sheath (8) is inserted into the rigid sheath (9);

a cap (7) is located at a front end of the flexible sheath (8);

the flexible sheath (8) has multiple channels therein along an axial direction thereof, including two pairs of traction channels, two traction channels of each pair are distributed symmetrically relative to a center of the flexible sheath (8), a connecting line of the two traction channels of each pair passes through a circle center of the flexible sheath (8), and the two pairs of traction channels are distributed in a cross manner;

the turning traction wires (10) pass through the traction channels and then are connected with the cap (7).

9. The multidirectional turning endoscope, as recited in claim 5, wherein:

the insertion portion (2) is a flexible sheath (8);

a cap (7) is located at a front end of the flexible sheath (8);

the flexible sheath (8) has multiple channels therein along an axial direction thereof, including two pairs of traction channels, two traction channels of each pair are distributed symmetrically relative to a center of the flexible sheath (8), a connecting line of the two traction channels of each pair passes through a circle center of the flexible sheath (8), and the two pairs of traction channels are distributed in a cross manner;

capillary support tubes (11) are respectively located within the two pairs of traction channels of the flexible sheath (8);

the turning traction wires (10) pass through the traction channels and the capillary support tubes (11) and then are connected with the cap (7).

10. The multidirectional turning endoscope, as recited in claim 5, wherein:

the insertion portion (2) comprises a flexible sheath (8) and a rigid sheath (9);

the flexible sheath (8) is inserted into the rigid sheath (9);

a cap (7) is located at a front end of the flexible sheath (8);

the flexible sheath (8) has multiple channels therein along an axial direction thereof, including two pairs of traction channels, two traction channels of each pair are distributed symmetrically relative to a center of the flexible sheath (8), a connecting line of the two traction channels of each pair passes through a circle center of the flexible sheath (8), and the two pairs of traction channels are distributed in a cross manner;

the turning traction wires (10) pass through the traction channels and then are connected with the cap (7).

11. The multidirectional turning endoscope, as recited in claim 1, wherein: one of the left conical cylinder and the right conical cylinder (20) is threadedly connected with the inner wall of the endoscope handle (4), an external surface of the one of the left conical cylinder and the right conical cylinder (20) has external screw threads, the inner wall of the endoscope handle (4) has internal threaded holes, and the external screw threads of the one of the left conical cylinder and the right conical cylinder are engaged with the internal threaded holes.

12. The multidirectional turning endoscope, as recited in claim 11, wherein:

the insertion portion (2) is a flexible sheath (8);

a cap (7) is located at a front end of the flexible sheath (8);

the flexible sheath (8) has multiple channels therein along an axial direction thereof, including two pairs of traction channels, two traction channels of each pair are distributed symmetrically relative to a center of the flexible sheath (8), a connecting line of the two traction channels of each pair passes through a circle center of the flexible sheath (8), and the two pairs of traction channels are distributed in a cross manner;

capillary support tubes (11) are respectively located within the two pairs of traction channels of the flexible sheath (8);

the turning traction wires (10) pass through the traction channels and the capillary support tubes (11) and then are connected with the cap (7).

13. The multidirectional turning endoscope, as recited in claim 11, wherein:

the insertion portion (2) comprises a flexible sheath (8) and a rigid sheath (9);

the flexible sheath (8) is inserted into the rigid sheath (9);

a cap (7) is located at a front end of the flexible sheath (8);

the flexible sheath (8) has multiple channels therein along an axial direction thereof, including two pairs of traction channels, two traction channels of each pair are distributed symmetrically relative to a center of the flexible sheath (8), a connecting line of the two traction channels of each pair passes through a circle center of the flexible sheath (8), and the two pairs of traction channels are distributed in a cross manner;

the turning traction wires (10) pass through the traction channels and then are connected with the cap (7).

14. The multidirectional turning endoscope, as recited in claim 1, wherein: two back ends of one pair of the turning traction wires are respectively fixed along the circumferential directions of the left turning wheel (17) with an interval of 180°, and two back ends of another pair of the turning traction wires are respectively fixed along the circumferential direction of the right turning wheel (18) with an interval of 180°.

15. The multidirectional turning endoscope, as recited in claim 14, wherein:

the insertion portion (2) is a flexible sheath (8);

a cap (7) is located at a front end of the flexible sheath (8);

the flexible sheath (8) has multiple channels therein along an axial direction thereof, including two pairs of traction channels, two traction channels of each pair are distributed symmetrically relative to a center of the flexible sheath (8), a connecting line of the two traction channels of each pair passes through a circle center of the flexible sheath (8), and the two pairs of traction channels are distributed in a cross manner;

capillary support tubes (11) are respectively located within the two pairs of traction channels of the flexible sheath (8);

the turning traction wires (10) pass through the traction channels and the capillary support tubes (11) and then are connected with the cap (7).

16. The multidirectional turning endoscope, as recited in claim 14, wherein:

the insertion portion (2) comprises a flexible sheath (8) and a rigid sheath (9);

the flexible sheath (8) is inserted into the rigid sheath (9);

a cap (7) is located at a front end of the flexible sheath (8);

the flexible sheath (8) has multiple channels therein along an axial direction thereof, including two pairs of traction channels, two traction channels of each pair are distributed symmetrically relative to a center of the flexible sheath (8), a connecting line of the two traction channels of each pair passes through a circle center of the flexible sheath (8), and the two pairs of traction channels are distributed in a cross manner;

the turning traction wires (10) pass through the traction channels and then are connected with the cap (7).

17. The multidirectional turning endoscope, as recited in claim 1, wherein:

the insertion portion (2) is a flexible sheath (8);

a cap (7) is located at a front end of the flexible sheath (8);

the flexible sheath (8) has multiple channels therein along an axial direction thereof, including two pairs of traction channels, two traction channels of each pair are distributed symmetrically relative to a center of the flexible sheath (8), a connecting line of the two traction channels of each pair passes through a circle center of the flexible sheath (8), and the two pairs of traction channels are distributed in a cross manner;

capillary support tubes (11) are respectively located within the two pairs of traction channels of the flexible sheath (8);

the turning traction wires (10) pass through the traction channels and the capillary support tubes (11) and then are connected with the cap (7).

18. The multidirectional turning endoscope, as recited in claim 1, wherein:

the insertion portion (2) comprises a flexible sheath (8) and a rigid sheath (9);

the flexible sheath (8) is inserted into the rigid sheath (9);

a cap (7) is located at a front end of the flexible sheath (8);

the flexible sheath (8) has multiple channels therein along an axial direction thereof, including two pairs of traction channels, two traction channels of each pair are distributed symmetrically relative to a center of the flexible sheath (8), a connecting line of the two traction channels of each pair passes through a circle center of the flexible sheath (8), and the two pairs of traction channels are distributed in a cross manner;

the turning traction wires (10) pass through the traction channels and then are connected with the cap (7).

\* \* \* \* \*